(12) United States Patent
Geiger et al.

(10) Patent No.: US 10,954,260 B2
(45) Date of Patent: Mar. 23, 2021

(54) CYMANQUINE COMPOUNDS AND DERIVATIVES THEREOF AND USES THEREOF

(71) Applicant: UNIVERSITY OF VERMONT AND STATE AGRICULTURAL COLLEGE, Burlington, VT (US)

(72) Inventors: William E. Geiger, Williston, VT (US); Kevin Lam, Genval (BE); Jon E. Ramsey, Richmond, VT (US); Claire F. Verschraegen, Burlington, VT (US)

(73) Assignee: University of Vermont and State Agricultural College, Burlington, VT (US)

(*) Notice: Subject to any disclaimer, the term of this patent is extended or adjusted under 35 U.S.C. 154(b) by 0 days.

(21) Appl. No.: 16/531,683

(22) Filed: Aug. 5, 2019

(65) Prior Publication Data

US 2020/0031856 A1     Jan. 30, 2020

Related U.S. Application Data

(62) Division of application No. 15/541,300, filed as application No. PCT/US2016/012050 on Jan. 4, 2016, now Pat. No. 10,370,395.

(60) Provisional application No. 62/099,335, filed on Jan. 2, 2015.

(51) Int. Cl.
    *C07F 13/00*         (2006.01)
    *A61K 45/06*         (2006.01)
    *A61K 31/555*       (2006.01)

(52) U.S. Cl.
    CPC ............ *C07F 13/00* (2013.01); *A61K 31/555* (2013.01); *A61K 45/06* (2013.01)

(58) Field of Classification Search
    CPC .............................. A61K 31/555; C07F 13/00
    See application file for complete search history.

(56) References Cited

U.S. PATENT DOCUMENTS 10,370,395 B2 *    8/2019    Geiger ................... A61K 45/06
10,512,652 B2 *   12/2019    Geiger ................ A61K 31/555

* cited by examiner

*Primary Examiner* — Golam M Shameem
(74) *Attorney, Agent, or Firm* — Hodgson Russ LLP

(57) ABSTRACT

Organometallic compounds comprising a chloroquinoline moiety and uses of the compounds. The compounds are, for example, manganese or rhenium complexes of a ligand comprising a chloroquinoline moiety. The compounds can be used in, for example, methods of inhibiting cell growth.

18 Claims, 10 Drawing Sheets

CYMANQUINE COMPOUNDS AND DERIVATIVES THEREOF AND USES THEREOF

CROSS-REFERENCE TO RELATED APPLICATIONS

This application is a divisional application of U.S. patent application Ser. No. 15/541,300, filed on Jun. 30, 2017, which is a National Stage Application of International Application No. PCT/US2016/012050, filed on Jan. 4, 2016, which claims priority to U.S. Provisional Patent Application No. 62/099,335, filed Jan. 2, 2015, the disclosures of which are incorporated herein by reference.

FIELD OF THE DISCLOSURE

The present disclosure generally relates to manganese and rhenium organometallic compounds comprising chloroquinoline-based ligands and use of the compounds, for example, to inhibit cell growth (e.g., treat cancer).

BACKGROUND OF THE DISCLOSURE

Chloroquine (CQ, 1) and hydroxychloroquine (HCQ) are known for their antimalarial activities and as inhibitors of autophagy in mammalian cells. However, their roles as anticancer agents are still emerging. Ferroquine (FQ, 2) and structurally-modified ferroquines have also been intensely studied as antimalarials. Ferroquine is mentioned as a possible antitumor agent in two recent papers (Reiter, C. et al. *Eur. J. Med. Chem.* 2014, 75, 403; Chellan, P. et al. *Dalton Trans.* 2014, 43, 513).

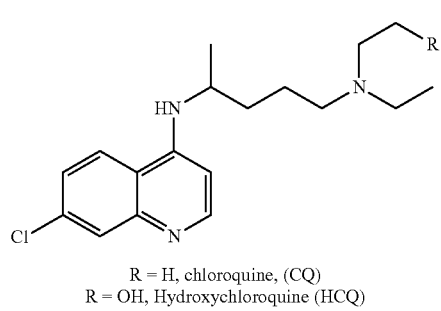

R = H, chloroquine, (CQ)
R = OH, Hydroxychloroquine (HCQ)

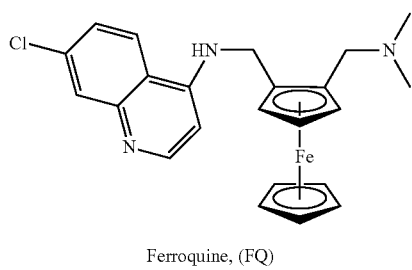

Ferroquine, (FQ)

Despite their promise, a recent scientific report has suggested that the ionization constants (pKa) for CQ and HCQ are too high for them to be effective lysosomotropic agents in bulky tumors that create low pH environments in their interiors (Pellegrini, et al. *Autophagy* 2014 10,1)

SUMMARY OF THE DISCLOSURE

The present disclosure provides novel organometallic compounds comprising a chloroquinoline moiety and compositions comprising one or more of the compounds. These compositions can be used to inhibit the growth of cells. In one aspect, the disclosure provides methods for inhibiting the growth of cells, such as cancer cells, using the present compounds or compositions.

A compound can have the following formula:

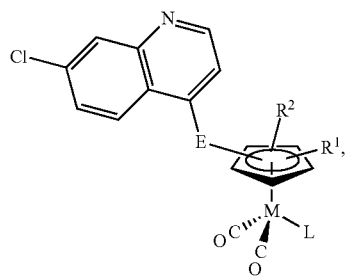

where: M is Mn or Re, L is a neutral, two-electron donor, $R^1$ is H or an amine-substituted alkyl group, $R^2$ is H, $(CH_2)_n CH_3$ (where n is 0, 1, 2 or any integer from 1 to 20), OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety.

For example, $R^1$ is $(CH_2)_n NR^3 R^4$, where n is an integer from 1 to 20 and $R^3$ and $R^4$ are independently H or an $C_1$-$C_x$ alkyl group, where x is an integer from 2 to 20. For example, L is selected from —CO, phosphines (e.g., alkyl phosphines, aryl phosphines, and alkyl aryl phosphines), phosphites (e.g., alkyl phosphites, aryl phosphites, and alkyl aryl phosphites), aryl amines (e.g., pyridine and its analogues substituted by standard functionalities such as halide or alkyl groups at the ortho and/or para position), alkynes, and carbenes. For example, E is —$NH(CH_2)_n$—, —$NH(CH_2)_n NH$— where n is an integer from 1 to 10. For example, a second CO ligand is replaced by a two-electron donor (e.g., a neutral, two-electron donor) described herein.

A composition can comprise one or more compounds and a pharmaceutical carrier. Examples of suitable pharmaceutical carriers are known in the art.

A method of alleviating the symptoms of cancer can comprises administering to an individual who has been diagnosed with, is suffering from, or is at risk of developing cancer comprising administering to the individual a therapeutically effective amount of a composition comprising one of more compounds or a composition. The method can further comprise subjecting the individual to one or more of the following: i) in cases where the individual has a malignant tumor, surgically removing a malignant tumor, ii) radiation, and iii) additional chemotherapy. Suitable surgical methods of removing a malignant tumor, radiation, and chemotherapy are known in the art.

A kit can comprises one or more containers or packaging having a compound or a composition and instructions for use. A kit can comprise a plurality of individualized sealed packets, each individual packets representing a dose of the composition for a single use.

BRIEF DESCRIPTION OF THE DRAWINGS

FIG. 1 is the $^1H$ spectrum, and FIG. 2 is the $^{13}C$ spectrum.

FIG. 3 is the $^1$H spectrum, and FIG. 4 is the $^{13}$C spectrum.

DESCRIPTION OF THE DISCLOSURE

Figure 1:
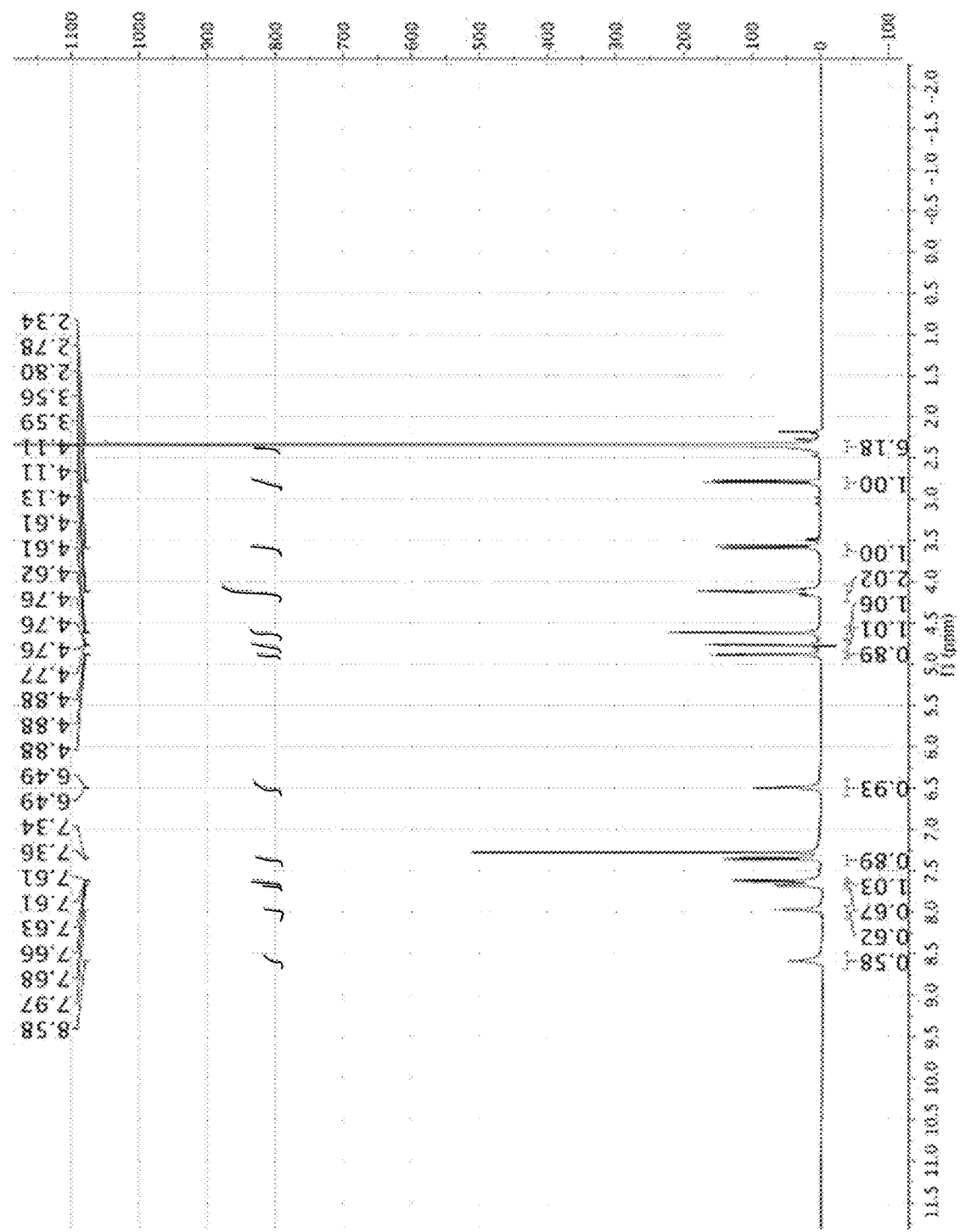
FIGS. 1 and 2 are NMR spectra of pure cymanquine (CMQ, 3) after chromatographic purification.

The present disclosure provides CMQ compounds and derivatives thereof, compositions comprising one or more of the compounds, and uses of such compounds. For example, the compounds can be used in methods of treating diseases such as cancer.

As used herein, the term "alkyl group," unless otherwise stated, refers to branched or unbranched hydrocarbons. Examples of such alkyl groups include methyl groups, ethyl groups, propyl groups, butyl groups, isopropyl groups, tert-butyl groups, and the like. For example, the alkyl group is a $C_1$ to $C_3$ alkyl group including all integer numbers of carbons and ranges of numbers of carbons therebetween. Alkyl groups may be substituted with various other functional groups. For example, the alkyl groups can be substituted with groups such as, for example, amines (acyclic and cyclic), alcohol groups, ether groups, and halogen atoms.

In an aspect, the present disclosure provides CMQ compounds and derivatives thereof. The compounds comprise $CpMn(CO)_{3-n}L_n$ or $CpRe(CO)_{3-n}L_n$ moieties, where Cp is a cyclopentadienyl ligand and n=0, 1, or 2. The Cp group of the $CpMn(CO)_{3-n}L_n$ or $CpRe(CO)_{3-n}L_n$ moieties may be substituted (e.g., with an amine-substituted alkyl group). L is linked to the Mn. The Cp group of the $CpMn(CO)_2L$ or $CpRe(CO)_2L$ moieties may be substituted (e.g., with an amine-substituted alkyl group). The Mn compounds can be referred to as cymantrene 'conjugates', which comprise cymantrene (cyclopentadienyl manganese tricarbonyl, $CpMn(CO)_3$, is called cymantrene) covalently bonded (i.e., conjugated to) a molecular moiety (i.e., a 'backbone') that has some biological relevance, e.g., a chloroquinoline moiety.

In one embodiment, the compound is Compound, 5, which has a —$CH_2NMe_2$ group in place of a hydrogen on the cyclopentadienyl ring. In one embodiment, the compound is the manganese derivative 3 or 4. The "pseudo-cymanquine" compound 4 lacks the cyclopentadienyl-$CH_2NMe_2$ group of CMQ.

In one embodiment, the compounds have the following structure:

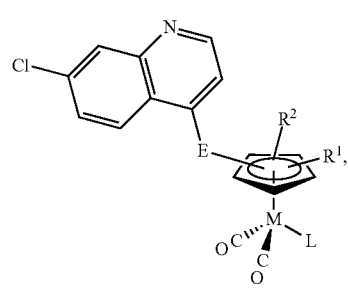

where M is Mn or Re. L is a neutral, two-electron donor (examples of suitable two-electron donors include —CO, phosphines (e.g., alkyl phosphines, aryl phosphines, and alkyl aryl phosphines), phosphites (e.g., alkyl phosphites, aryl phosphites, and alkyl aryl phosphites), aryl amines (e.g., pyridine and its analogues substituted by standard functionalities such as halide or alkyl groups at the ortho and/or para position), alkynes, and carbenes), $R^1$ is H or an amine-substituted alkyl group, and $R^2$ is H, $(CH_2)_nCH_3$ (n=0, 1, 2 or higher. In one embodiment, n is an integer from 1 to 10), OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I.

In one embodiment, $R^1$ is —$(CH_2)_nNR^3R^4$, where n is 1 or higher, and $R^3$ and $R^4$ are independently H or an $C_1$-$C_x$ alkyl group, wherein x is 2 or higher). In one embodiment, n is any integer from 1 to 20 and x is any integer from 2 to 20. In one embodiment, n is any integer from 1 to 10 and x is any integer from 2 to 10.

E is a linker moiety connecting the cyclopentadienyl moiety with the chloroquinoline moiety. Examples of suitable linker moieties include —$NH(CH_2)_n$—, —$NH(CH_2)_n$NH— (where n is 1, 2 or higher. In one embodiment, n is any integer from 1 to 10).

In one embodiment, L is a water-soluble phosphine. Suitable water-soluble phosphines are known in the art.

In one embodiment, the compounds do not have the following structure:

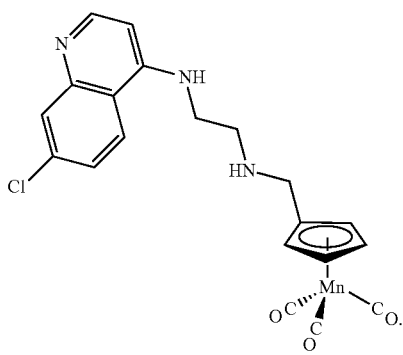

In different embodiments, the compound has the following structures:

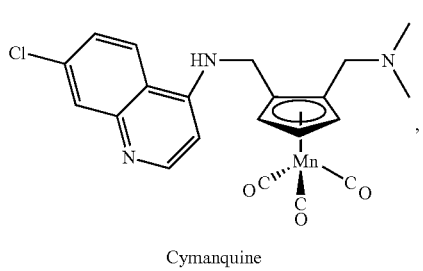

Cymanquine

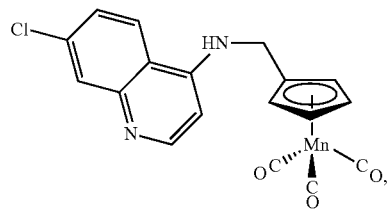

Pseudo-cymanquine

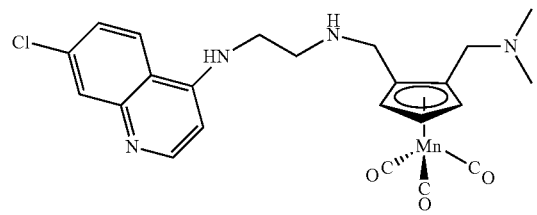

The present disclosure includes all possible stereoisomers and geometric isomers of all the compounds. The present disclosure includes both racemic compounds and optically active isomers. When a compound is desired as a single enantiomer, it can be obtained either by resolution of the final product or by stereospecific synthesis from either isomerically pure starting material or use of a chiral auxiliary reagent. For example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of a compound are possible, the present disclosure is intended to include all tautomeric forms of the compounds.

Compounds of the disclosure can exist as salts. In one embodiment, pharmaceutically acceptable salts of the compounds of the disclosure may be used. As used herein, the term "pharmaceutically acceptable salts" refers to salts or zwitterionic forms of the compound or compounds. In one embodiment, any type of salt may be used such as, for example, tetrakis(perfluorophenyl)borate salts. Salts of the compound or compounds can be prepared during the final isolation and purification of the compounds or separately by reacting the compound with an acid having a suitable cation. The pharmaceutically acceptable salts of the compound or compounds are acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, p-toluenesulfonate, and tetrakis(perfluorophenyl)boratesalts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present disclosure appearing herein is intended to include the compounds as well as pharmaceutically acceptable salts, hydrates, or prodrugs thereof.

In one embodiment, a compound or combination(s) of the compounds can be used as molecular tags (e.g., redox molecular tags). For example, the tags are referred to as piano-stool redox tags. The compound or multiple compounds (the same or different compounds) are covalently bonded to a drug (e.g., small molecule drug or biological drug such as a protein or peptide).

In one embodiment, a molecular "tag" may be appended to the present molecules. Tags may be selected that have desirable chemical, physical, or analytical properties. In one embodiment, metal carbonyl appendages having strong IR activity in an otherwise biologically silent region may be used.

In one embodiment, a diverse "tag toolbox" can be used to address the breadth of chemical, biological, and analytical needs. The MCp(CO)$_2$L system (M=Mn, Re; L=CO or other two-electron ligand (e.g., a neutral two-electron ligand) described herein) offers desirable possibilities owing principally to its very strong, charge-sensitive, carbonyl IR absorptions, as well as a range of other spectroscopic possibilities. Compounds of the type $M(\eta^5-C_5H_4R)(CO)_2L$ are either commercially available or easily prepared. Here, $(\eta^5-C_5H_4R)$ refers to a Cp ring in which a hydrogen atom has been replaced by another atom or group R. These complexes have outstanding air- and thermal-stability, and undergo the types of chemistry at the five-membered ring that are known in the art to allow tag-attachment of the ferrocenyl group. In one embodiment, a ligand L is introduced to further modify the properties of the tag, for example by replacing a carbonyl with a donor ligand that modulates the oxidative redox potential or provides water-solubility for biological applications. In one embodiment, a second two-electron ligand, L or L', could be added, replacing another CO ligand. This further changes the physical and chemical properties of the complexes, but retains their strong IR activity owing to the remaining CO ligand.

In one embodiment, to enhance the solubility of the complexes in aqueous solutions, derivatives can be prepared in which a CO is replaced by a water-solubilizing phosphine ligand. The neutral form of the compound is slightly soluble in DMSO and in water. The hydrochloride salt is much more soluble in water. The compound could be stored at room temperature without noticeable degradation over a period of at least 6 months. In one embodiment, the compounds or compositions comprising the compounds are stored protected from light, such as in the dark.

The compounds or a combination of the compounds can be used to treat or alleviate the symptoms of diseases. For example, the compounds can be used in the treatment of diseases such as cell proliferative disorders (e.g., cancer).

The language "therapeutically effective amount" of a compound of the disclosure refers to an amount of an agent which is effective, upon single or multiple dose administration to an individual for alleviating the symptoms of, or treating a disease (e.g., cell proliferation disorder) or in prolonging the survivability of the patient with such diseases beyond that expected in the absence of such treatment. The exact amount desired or required will vary depending on the particular compound or composition used, its mode of administration and the like. Appropriate effective amount can be determined by one of ordinary skill in the art informed by the instant disclosure using only routine experimentation.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

In one embodiment, the present disclosure provides a composition comprising one or more compounds of the present disclosure. Compositions comprising one or more compounds of the present disclosure include, for example, pharmaceutical preparations.

Accordingly, the present disclosure further provides pharmaceutical formulations comprising the compound or compounds, or a pharmaceutically acceptable salt, prodrug, or hydrate thereof, together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

Examples of pharmaceutically-acceptable carrier include pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

Compositions comprising a compound of the disclosure and a pharmaceutical agent can be prepared at a patient's bedside, or by a pharmaceutical manufacture. In the latter case, the compositions can be provided in any suitable container, such as a sealed sterile vial or ampule, and may be further packaged to include instruction documents for use by a pharmacist, physician or other health care provider. The compositions can be provided as a liquid, or as a lyophilized or powder form that can be reconstituted if necessary when ready for use. In particular, the compositions can be provided in combination with any suitable delivery form or vehicle, examples of which include, for example, liquids, caplets, capsules, tablets, inhalants or aerosol, etc. The delivery devices may comprise components that facilitate release of the pharmaceutical agents over certain time periods and/or intervals, and can include compositions that enhance delivery of the pharmaceuticals, such as nanoparticle, microsphere or liposome formulations, a variety of which are known in the art and are commercially available. Further, each composition described herein can comprise one or more pharmaceutical agents. The compositions described can include one or more standard pharmaceutically acceptable carriers. Some examples herein of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art can be used to introduce (i.e., administer) the compositions of the disclosure to an individual. For example, a compound or mixture of compounds, or compositions containing one or more compound, can be administered in any manner including, but not limited to, orally, parenterally, sublingually, transdermally, rectally, transmucosally, topically, via inhalation, via buccal administration, or combinations thereof. Parenteral administration includes, but is not limited to, intravenous, intraarterial, intracranial, intradermal, subcutaneous, intraperitoneal, subcutaneous, intramuscular, intrathecal, and intraarticular. The compound(s) also can be administered in the form of an implant, which allows a slow release of the compound(s), as well as a slow controlled i.v. infusion.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In certain embodiments, the methods of the disclosure include administering to a subject a therapeutically effective amount of a compound or compounds in combination with another pharmaceutically active ingredient. Examples of pharmaceutically active ingredients known to treat cell proliferative disorders include anticancer agent, antiproliferative agent, chemotherapeutic agents. Other pharmaceutically active ingredients that may be used can be found in Harrison's Principles of Internal Medicine, Thirteenth Edition, Eds. T. R. Harrison et al. McGraw-Hill N.Y., NY; and the Physicians Desk Reference 50th Edition 1997, Oradell N.J., Medical Economics Co., Formulary, 2012; 252-256, the complete contents of which are expressly incorporated herein by reference. A compound or compounds and the pharmaceutically active ingredient may be administered to the subject in the same pharmaceutical composition or in different pharmaceutical compositions (at the same time or at different times).

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment.

The individual for administration of the present compounds and compositions may be human or may be a non-human animal. For veterinary use, a compound or compounds, or a pharmaceutically acceptable salt, is administered as a suitably acceptable formulation in accordance with normal veterinary practice. The veterinarian can readily determine the dosing regimen and route of administration that is most appropriate for a particular animal. Animals treatable by the present compounds and methods include pets, farm animals and the like.

The present compounds and compositions may be used with other therapeutic or diagnostic agents or even with other modalities of treatment such as radiation or surgery. When combined with other therapeutic or diagnostic agents or modalities, the combination may be administered or carried out simultaneously or sequentially within a short period of time (i.e., hours) or over a longer period of time (i.e., days or months).

The present compositions and compounds may be administered to an individual who has been diagnosed with a cell proliferative disorder or a related condition or to individuals who are at risk of developing such condition or disease. For example, the compositions or compounds may be administered to an individual who may be at risk of developing cancer due to predisposition or genetic factors or the like.

The present compounds and compositions may be useful for a wide variety of cancers that have been shown to engage in autophagy as a means of survival. In one embodiment, the cancer may be carcinoma/sarcoma of the brain, breast, pancreas, prostate, colon, kidney, and skin. In one embodiment, the cancer may be leukemia.

In an aspect, the disclosure provides a packaged composition including a therapeutically effective amount of a compound or compounds and a pharmaceutically acceptable carrier or diluent. The compositions may be packaged with instructions to treat one or more individuals suffering from or susceptible to a cell proliferative disorder. Similarly, in one embodiment, kits may be provided which include a compound or compounds, pharmaceutically acceptable esters, and salts thereof, and instructions for use.

The following examples further describe the disclosure. These examples are intended to be illustrative and not limiting in any way.

Example 1

The following is an example of the synthesis of CMQ and derivatives thereof.

Preparation of CMQ, 3 (Mixture of 2 Isomers)

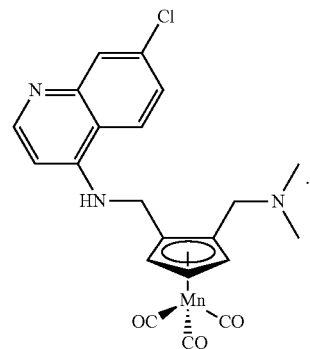

α-Formyl-(N,N-dimethylaminomethyl)cymantrene was synthetized following a known procedure. Loim, N. M., Abramowa, N. A., Parnes, Z. N., Kursanow, D. N., *J. Organomet. Chem.*, 1979, 168, C33.

α-Formyl-(N,N-dimethylaminomethyl)cymantrene (1.12 g, 3.87 mmol, 1 eq) was dissolved in 40 mL of dry methanol at 0° C. Then, sodium borohydride (0.322 g, 8.52 mmol, 2.2 eq) was added by portion over 15 minutes and the solution was allowed to come back to room temperature. After 2 hours, most of the solvent was removed under reduced pressure and the mixture was dissolved in 30 mL of dichloromethane. The organic solution was washed 2 times with 30 mL of water, then the organic layer was isolated, dried over magnesium sulfate, filtered and the solvent removed under reduced pressure. α-hydroxymethyl-(N,N-dimethylaminomethyl)cymantrene was obtained in a 67% yield as dark brown oil and was pure enough to be used as it was in the next step.

To a solution of α-hydroxymethyl-(N,N-dimethylaminomethyl)cymantrene (50 mg, 0.172 mmol, 1 eq) in 1 mL of dry THF, were added phthalimide (32.3 mg, 0.22 mmol, 1.28 eq) and triphenylphosphine (57.6 mg, 0.22 mmol, 1.28 eq). Then diisopropyl diazene-1,2-dicarboxylate (DIAD) (47 μL, 0.22 mmol, 1.28 eq) was added. After an hour, the solvent was removed and replaced by 0.5 mL of methanol. Then hydrazine hydrate (24 μL, 0.32 mmol, 1.82 eq) was added and the solution was stirred at room temperature for 30 minutes. 10 mL of a 1 N solution of HCl was added and the solution was quickly extracted three times with 10 mL of ethyl acetate. The pH of the aqueous layer was then increased to 13 by addition of a solution of 1 N NaOH and extracted 3 times with 10 mL of dichloromethane. The organic layers were combined, dried over magnesium sulfate and the solvent removed under reduced pressure to yield the desired α-aminomethyl-(N,N-dimethylaminomethyl)cymantrene which was used as it was in the next step. (26.2 mg).

Figure 2:
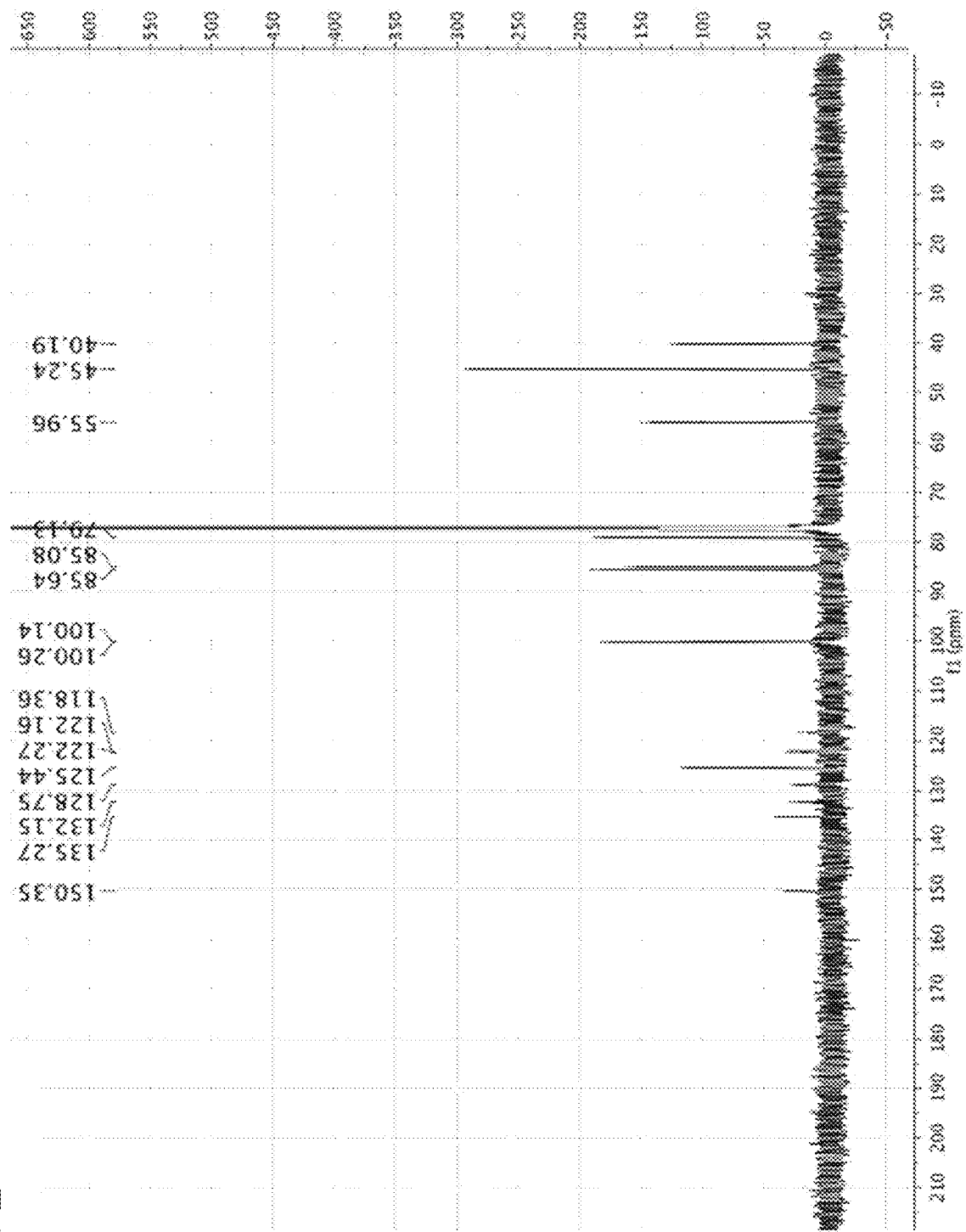

The crude α-aminomethyl-(N,N-dimethylaminomethyl)cymantrene (26.2 mg, 0.090 mmol, 1 eq) was dissolved in 2 mL of dry and degassed propanol and 7-chloro-4-fluoroquinoline (17.2 mg, 0.095 mmol, 1.05 eq). The solution was refluxed under nitrogen overnight after which the solvent was removed under reduced pressure and the compound purified by column chromatography over silica gel using AcOEt 1/Hexane 9 as the eluent. A light brown powder was obtained (16% yield over 3 steps). See FIGS. 1 and 2 for NMR spectra.

$^1$H NMR (500 MHz, CDCl$_3$): 2.34 (s, 6H), 2.79 (d, J=12.9 Hz, 1H), 3.58 (d, J=12.9 Hz, 2H), 4.08-4.16 (m, 2H), 4.61 (t, J=2.75 Hz, 1H), 4.76-4.77 (m, 1H), 4.88 (m, 1H), 6.40 (s, 1H), 7.35 (d, J=8.9 Hz, 1H), 7.62 (d, J=8.9 Hz, 1H), 7.66-7.68 (m, 1H), 7.97 (s, 1H), 8.58 (s, 1H).

$^{13}$C NMR (500 MHz, CDCl$_3$): 40.2, 45.2, 56.0, 79.1, 85.1, 85.7, 100.1, 100.3, 118.4, 122.2, 122.3, 125.5, 128.7, 132.1, 135.3, 150.3.

MSCl+m/z (%): 455.1 (8), 454.1 (30), 453.2 (24), 452.2 (100), 418.2 (2), 274.1 (2), 54.8 (3).

IR (neat) ν$_{max}$/cm$^{-1}$: 632, 668, 807, 840, 1135, 1426, 1577, 1913, 1939, 2011, 2831, 2950.

Anal. Calcd for C$_{21}$H$_{19}$ClMnN$_3$O$_3$: C, 55.83; H, 4.24; N, 9.30. Found: C, 56.25; H, 4.34; N, 9.43.

Preparation of Pseudo-Cymanquine, 4

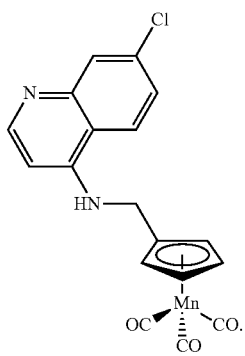

Aminomethylcymantrene was prepared following a known procedure. Telegina, L. N., Ezemitskaya, M. G., Godovikov, I. A., Babievskii, K. K., Loshin, B. V., Strelkova, T. V., Borisov, Y. A., Loim, N. M., *Eur. J. Inorg. Chem.*, 2009, 3636.

Figure 3:
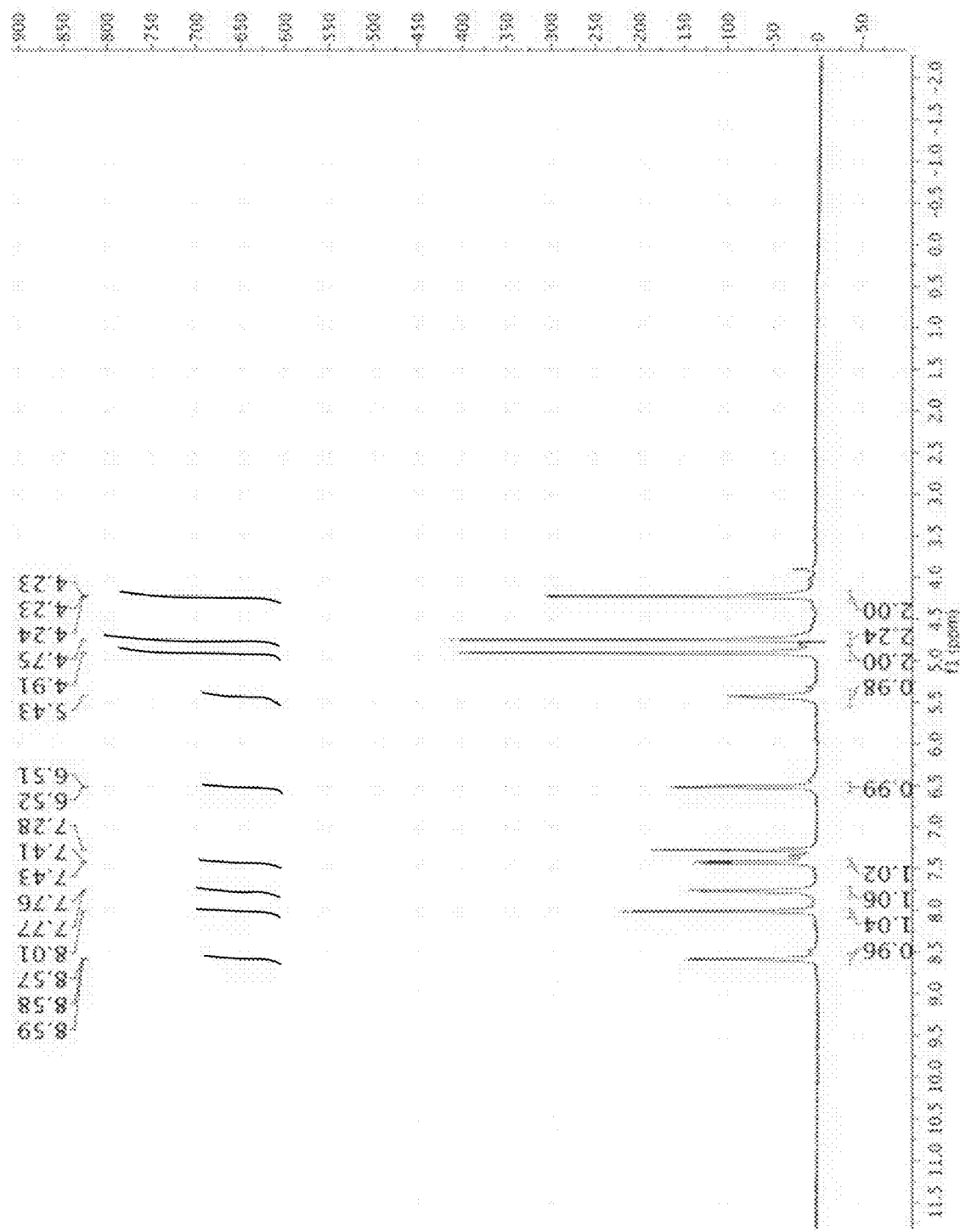
FIGS. 3 and 4 are NMR spectra of pure pseudo-cymanquine (4) after chromatographic purification.
Figure 4:
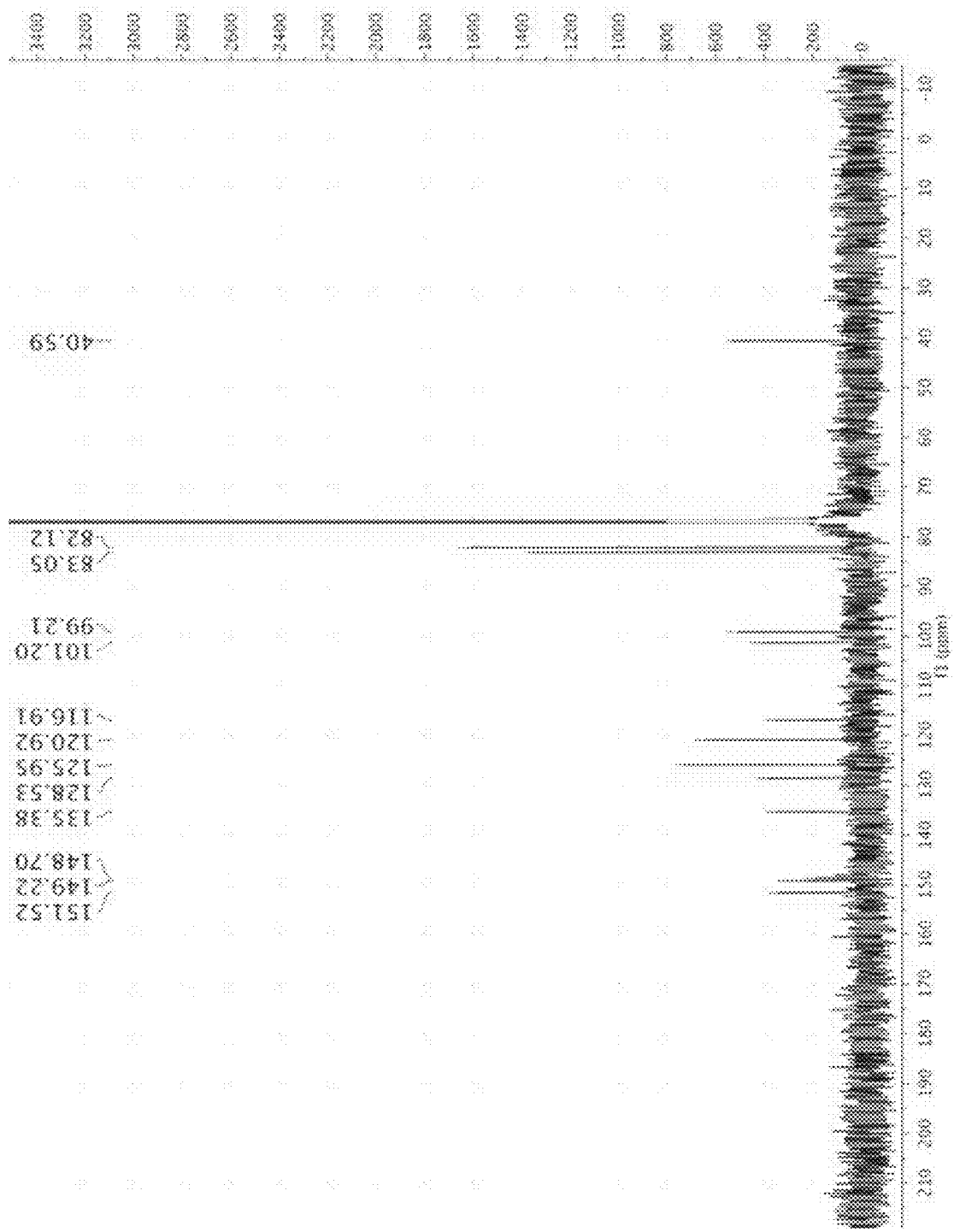

Aminomethylcymantrene (100 mg, 0.429 mmol, 1 eq) was dissolved in 5 mL of dry and degassed propanol and 7-chloro-4-fluoroquinoline (82 mg, 0.450 mmol, 1.05 eq). The solution was refluxed under nitrogen overnight after which the solvent was removed under reduced pressure and the compound purified by column chromatography over silica gel using AcOEt 1/Hexane 9 as the eluent. A light brown powder was obtained (67% yield). See FIGS. 3 and 4 for NMR spectra.

$^1$H NMR (500 MHz, CDCl$_3$): 4.23 (s, 2H), 4.75 (s, 2H), 4.91 (s, 2H), 5.43 (s, 1H), 6.51-652 (m, 1H), 7.42 (d, J=8.9 Hz, 1H), 7.77 (d, J=8.9 Hz, 1H), 8.01 (s, 1H), 8.57-8.59 (m, 1H)

$^{13}$C NMR (500 MHz, CDCl$_3$): 40.6, 82.1, 83.0, 99.2, 101.2, 116.9, 120.9, 125.9, 128.5, 135.4, 148.7, 149.2, 151.5.

MSCl+m/z (%): 397.8 (3), 396.8 (15), 395.9 (8), 394.8 (42), 346.8 (14), 297.0 (14), 254.9 (5), 224.9 (13), 224.0 (22), 223.0 (100).

IR (neat) ν$_{max}$/cm$^{-1}$: 630, 664, 848, 1139, 1567, 1569, 1883, 1901, 1927, 2010.

Anal. Calcd for C$_{18}$H$_{12}$ClMnN$_2$O$_3$: C, 54.78; H, 3.06; N, 7.10 Found: C, 55.35; H, 3.11; N, 7.11.

Preparation of 5

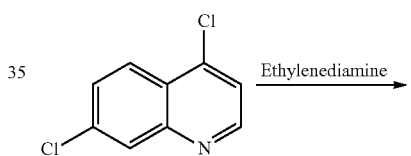

Dichloroquinoline (2 g, 10.10 mmol, 1 eq) was reacted with ethylenediamine (3.4 mL, 50.5 mmol, 5 eq) in 100 mL of xylene. The reaction mixture was refluxed overnight and then allowed to come back to room temperature. Most of the solvent was removed under reduced pressure and the mixture was dissolved in 30 mL of dichloromethane. The organic solution was washed twice with 30 mL of water, then the organic layer was isolated, dried over magnesium sulfate, filtered and the solvent removed under reduced pressure, yielding quantitatively the pure N1-(7-chloroquinolin-4-yl)ethane-1,2-diamine.

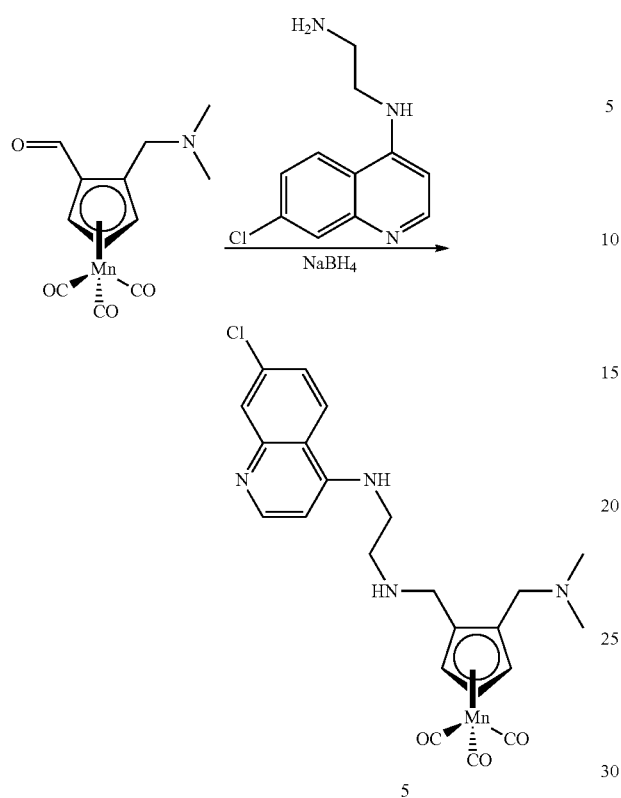

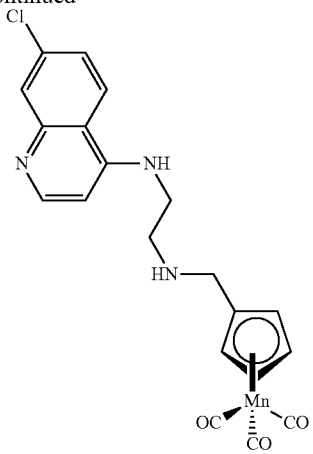

Compound 6 was prepared in a similar manner as 5 but by using formylcymantrene instead of α-Formyl-(N,N-dimethylaminomethyl)cymantrene.

Example 2

The following is an example of the characterization of CMQ and derivatives thereof.

Anodic Electrochemistry of CMQ Family. The electrochemical behavior of the three manganese compounds shown below was studied.

α-Formyl-(N,N-dimethylaminomethyl)cymantrene (0.1 g, 0.346 mmol, 1 eq) and N1-(7-chloroquinolin-4-yl)ethane-1,2-diamine (0.084 g, 0.380 mmol, 1.1 eq) were dissolved in 4 mL of dry methanol. The solution was refluxed for 5 hours and then down to 0° C. Sodium borohydride (0.088 g, 0.414 mmol, 1.2 eq) was added by portion over 15 minutes and the solution was allowed to come back to room temperature. After 2 hours, most of the solvent was removed under reduced pressure and the mixture was dissolved in 5 mL of dichloromethane. The organic solution was washed twice with 5 mL of water, after which the organic layer was isolated, dried over magnesium sulfate, filtered and the solvent removed under reduced pressure. Compound 5 was obtained in a 59% yield as yellowish solid and was pure enough to be used as it was. An analytically pure sample could be obtained by a quick filtration over silica gel using AcOEt 1/Hexane 9 as the eluent.

Preparation of 6

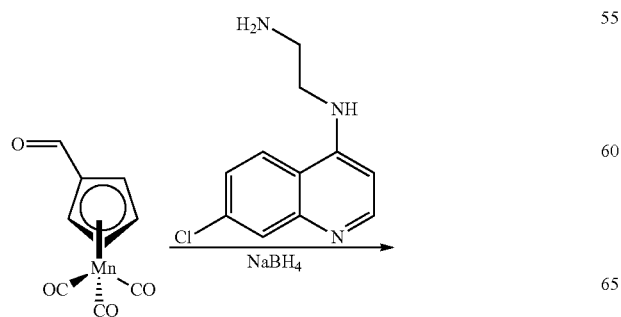

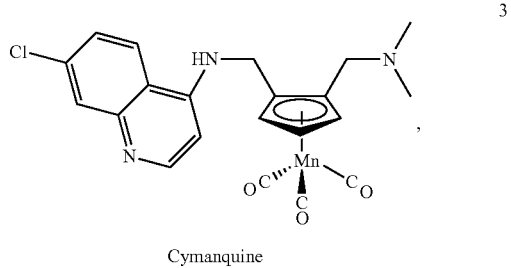

Cymanquine

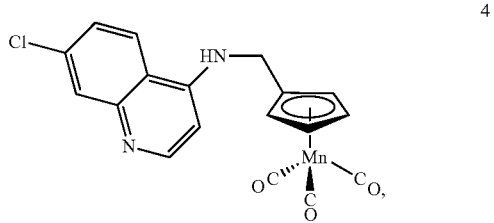

Pseudo-cymanquine

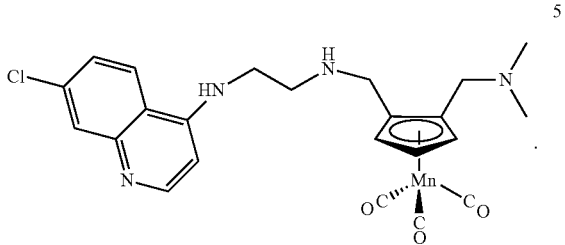

Electrochemical studies were carried out. The electrolyte solution used for these studies, namely dichloromethane with 0.05 M [NBu$_4$][B(C$_6$F$_5$)$_4$] as the supporting electrolyte, is known to provide an optimum medium for the electrochemical oxidation of compounds containing the MnCp(CO)$_3$ (Cp=η$^5$-C$_5$H$_5$) backbone (Laws et al., *J. Am. Chem. Soc.* 2008, 130, 9859). The potentials given here are referred to the ferrocene/ferrocenium reference couple. The experiments were carried out in a controlled atmosphere which minimizes exposure to oxygen and water. We refer to two types of standard electrochemical techniques that are commonly described in books on electrochemistry: cyclic voltammetry and bulk electrolysis (Bard, A. J.; Faulkner, L. R. *Electrochemical Methods*, John Wiley & Sons, New York, 2001, second edition) The former is useful for the analytical and gross mechanistic aspects of the electron-transfer properties of a compound, whereas the latter is most often employed for the electro-synthetic function of making isolable quantities of electrochemical oxidation or reduction products.

Anodic oxidation of the three compounds was investigated. They shared the basic character of having two consecutive one-electron oxidation processes, at the potentials given in the table. In each case, the first oxidation, at the potential $E_p(1)$, was a chemically irreversible one-electron process [$E_p$ refers to the peak potential of the voltammetric wave]. This means that the first one-electron oxidation product, e.g., 3$^+$, reacted rapidly to give a new compound, referred to here as the "follow-up" product, that is responsible for the second oxidation process at the potential E(2). The follow-up product was identified as having a structure in which the ring-nitrogen of the chloroquine moiety was protonated. This is shown below for CMQ as 3H$^+$.

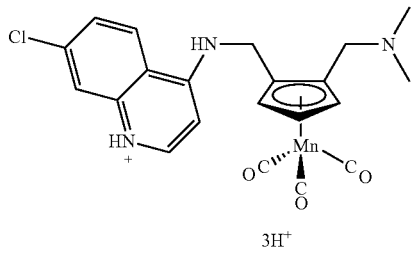

3H$^+$

The quinoline-protonated product is apparently formed by a reaction in which the initially formed radical cation, e.g., 3+, abstracts a hydrogen atom from the solvent. In all three systems, the potential $E_p(1)$ is at a value expected for the oxidation of the chloroquine moiety, and the second oxidation, E(2), is at a potential consistent with the one-electron oxidation of the cymantryl moiety, i.e., the MnCp(CO)$_3$ part of the molecule.

In the case of compound 4, the cyclic voltammograms show that the doubly-oxidized compound is persistent over the lifetime of the scan, which is of the order of 5-10 sec under our conditions. Thus, the oxidative electron-transfer reactions of 4 follow Eq 1, where SH=solvent:

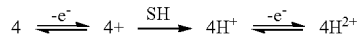

This oxidation mechanism was confirmed by bulk anodic electrolysis of 4, bulk cathodic electrolysis of 4H (which regenerated 4 by electron-induced deprotonation of 4H$^+$), and by acid/base studies. For compound 3, the first oxidation again involved protonation of the quinoline-ring nitrogen in a follow-up reaction. The protonated product 3H was isolated and its structure confirmed by NMR spectroscopy. In the case of both 3 and 5, the second oxidation was chemically irreversible, and the follow-up products of the second oxidations have not yet been identified. Equation 2 gives the known aspects of the anodic oxidation of 3.

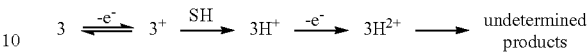

Table of potentials (vs ferrocene/ferrocenium (FcH)) measured by cyclic voltammetry for oxidation of compounds 3, 4, and 5 in dichloromethane/0.05 M [NBu$_4$][B(C$_6$F$_5$)$_4$]. $E_{1/2}$ is given for a chemically reversible process and the anodic peak potential, $E_p$, is given for an irreversible process.

| Compound | $E_p(1)$ (V vs FcH) | $E_{1/2}(2)$ or $E_p(2)$ (V vs FcH) | Comments |
|---|---|---|---|
| 3 | 0.82 | 1.25 ($E_p$) | |
| 4 | 1.14 | 1.35 ($E_{1/2}$) | 2$^{nd}$ oxdn partly reversible |
| 5 | 0.80 | 1.0 ($E_p$) | |

Figure 7:
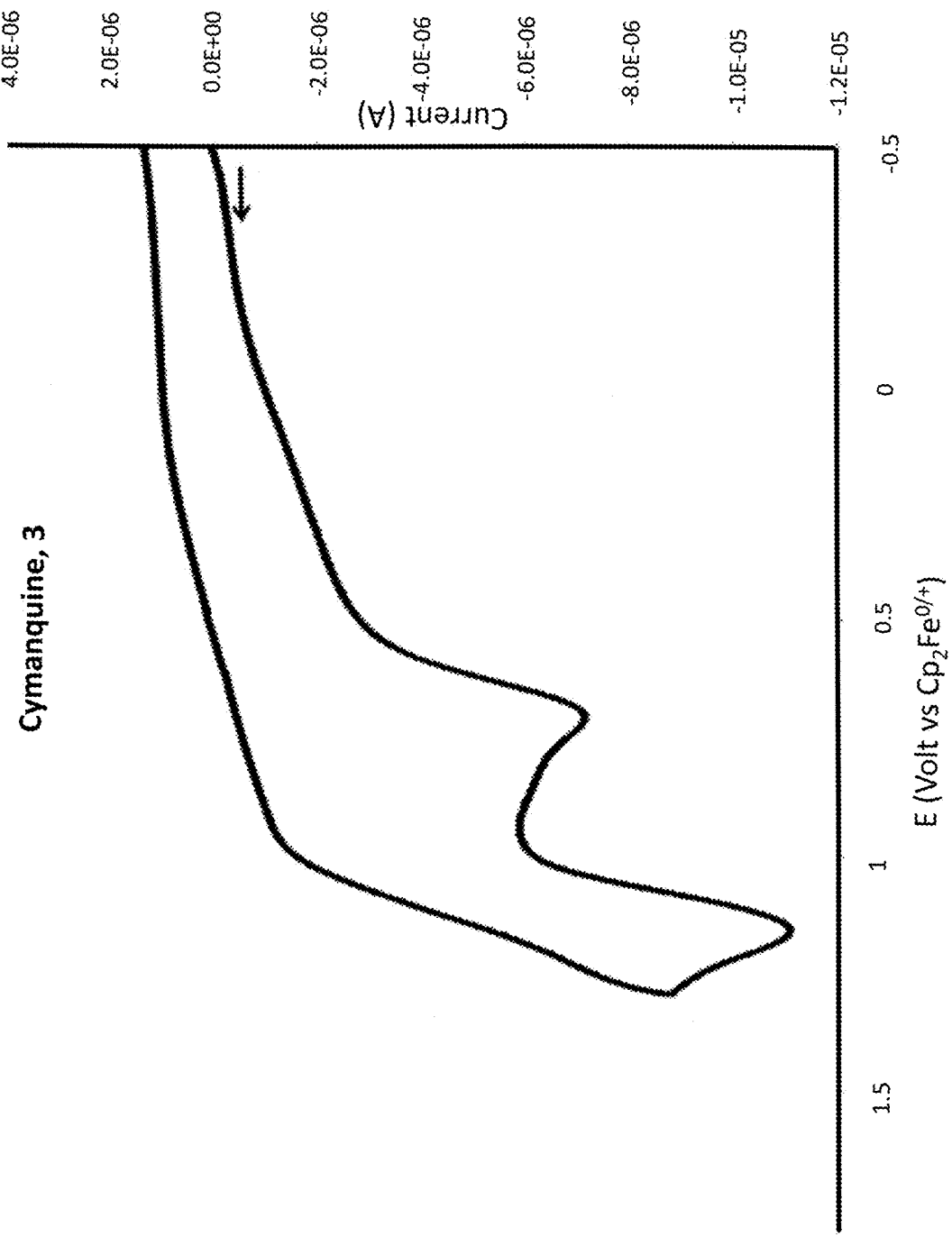
FIG. 7. Cyclic voltammetry scan recorded at a glassy carbon electrode for a solution of CMQ, 3, in dichloromethane containing 0.05 M $[NBu_4][B(C_6F_5)_4]$ as supporting electrolyte.
Figure 8:
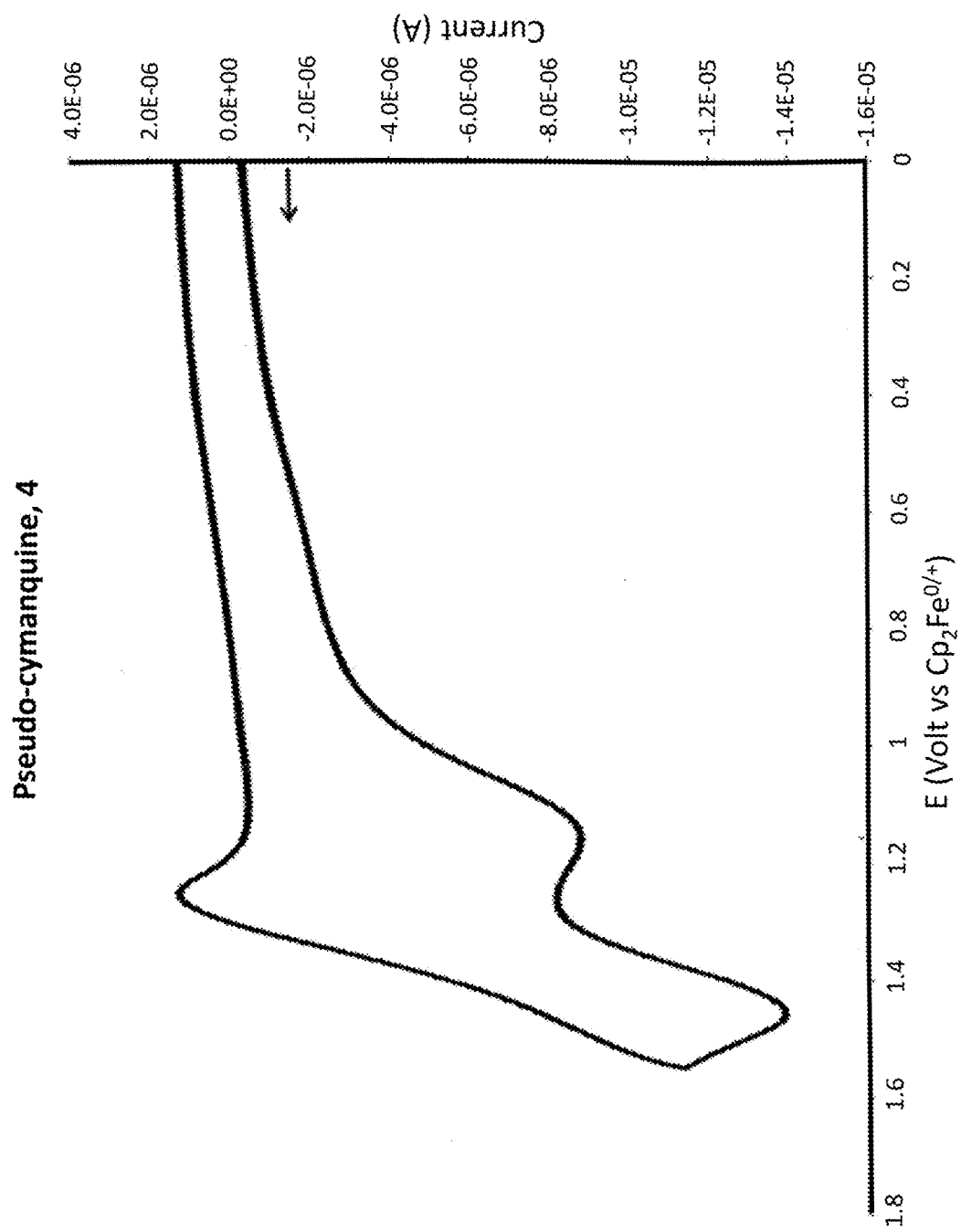
FIG. 8. Cyclic voltammetry scan recorded at a glassy carbon electrode for a solution of pseudo-cymanquine, 4, in dichloromethane containing 0.05 M $[NBu_4][B(C_6F_5)_4]$ as supporting electrolyte.
Figure 9:
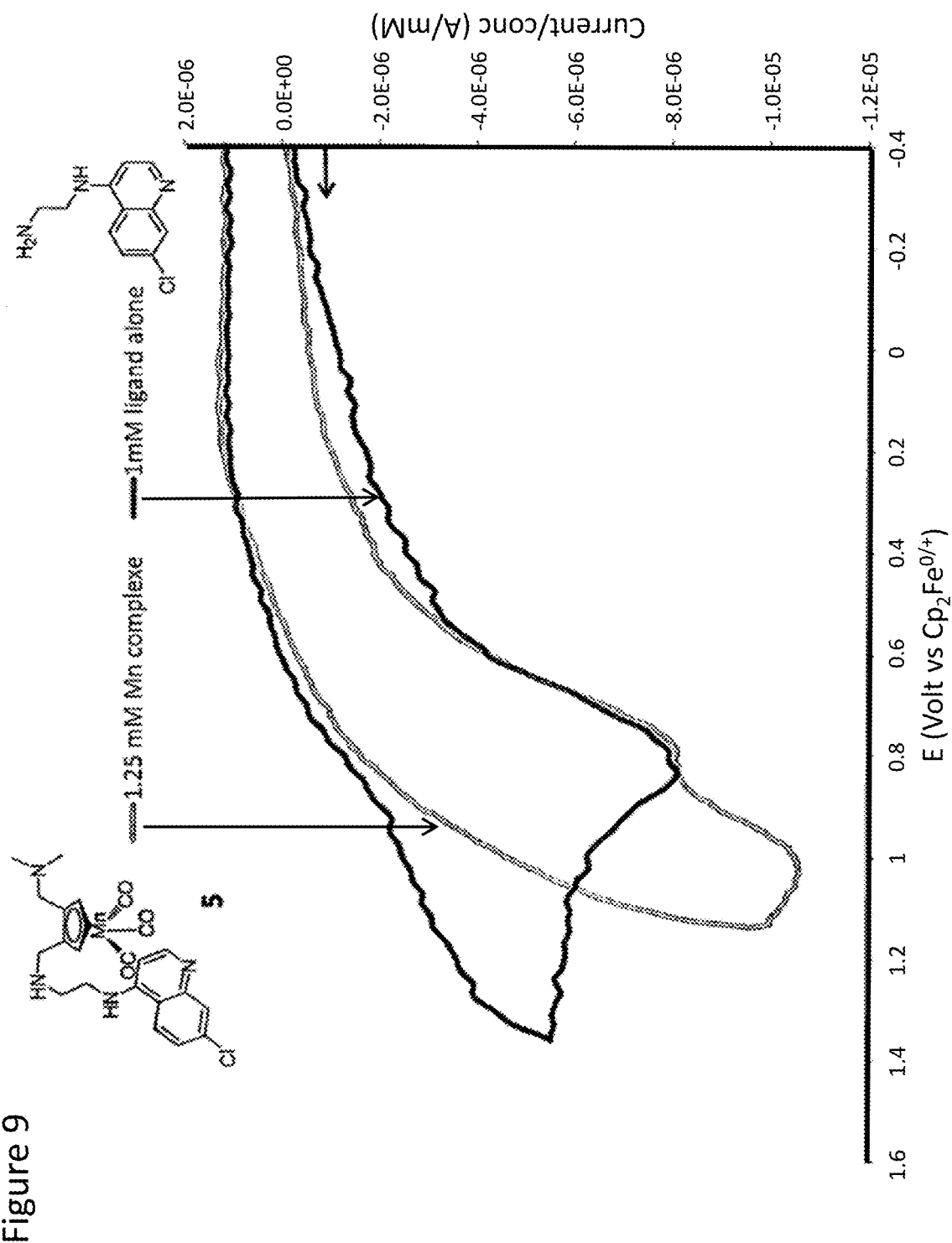
FIG. 9. Superposition of cyclic voltammetry scans recorded at a glassy carbon electrodes for solutions of either the manganese compound 5, or the chloroquine-like "free ligand" in dichloromethane containing 0.05 M $[NBu_4][B(C_6F_5)_4]$ as supporting electrolyte.

The electrochemical results demonstrate that the "cymanquine" family of compounds may be converted to proton-reactive species when they are exposed to positive potentials in the electrolyte medium. Standard electroanalytical methodologies may be employed, using simple carbon electrodes, for quantitative analysis of the compounds. These would include, but not be limited to, cyclic voltammetry (FIGS. 7, 8 and 9), square wave voltammetry, differential pulse voltammetry, and stripping voltammetry.

Example 3

The following is an example of the use of CMQ and derivatives thereof to treat cancer.

Materials and Methods. Cell lines and reagents. Human cancer cell lines ACHN (kidney adenocarcinoma), BxPC3 (pancreatic adenocarcinoma), DU145 (prostate carcinoma), HT29 (colorectal adenocarcinoma), Jurkat (T-cell lymphoma), LNCaP (androgen sensitive prostate adenocarcinoma), PC3 (androgen insensitive prostate adenocarcinoma), SB1A (melanoma), and T47D (breast infiltrating ductal carcinoma) were cultured RPMI 1640 (Mediatech, Inc., Manassas, Va.) supplemented with 10% fetal bovine serum, 1% penicillin/streptomycin/amphotericin B solution, 1 mM sodium pyruvate, 1% MEM non-essential amino acid solution, and 2 mM L-glutamine at 37° C. in a 5% CO2, humidified incubator. All supplements were purchased from HyClone™ (Logan, Utah). The HPV-18-transformed normal human prostate epithelium cell line, RWPE-1 was cultured in Keratinocyte-SFM supplemented with 5 ng/mL human recombinant epidermal growth factor, and 50 μg/mL bovine pituitary extract (Life Technologies) at 37° C. in a 5% CO2, humidified incubator. To achieve low pH conditions, aqueous 1, 4-piperazinediethanesulfonic acid (PIPES, Sigma Life Science) pH 6.23 was added to a final concentration of 50 mM in growth media. The resulting pH was measured to be 6.72±0.06 in the absence of cells. This concentration of PIPES showed no discernible effects on cell viability or growth rate over a 48 h period in the cell lines tested, with the exception of RWPE-1. Therefore, reduced pH conditions were not employed for this cell line. Chloroquine (CQ) diphosphate (MP Biomedicals, LLC.) stock solutions were prepared in water at a concentration of 33 mM and stored at −20° C. protected from light for no longer than 6 months. CMQ was prepared in dimethylsulfoxide (DMSO, Fisher Scientific) at a concentration of 33 mM and stored at −20° C. protected from light for no longer than 3 months.

Cytotoxicity assay. Cells were plated in 96-well tissue culture plates (Falcon) at a density of 2,000-5,000 cells per well (depending upon growth rate of cell line) in a volume of 100 µL growth media. Adherent cell lines were given 24 hours to adhere prior to removal of media and addition of serial dilutions (a total of 12, two-fold dilutions made from a 200 µM starting point, or 0.6% DMSO for the vehicle control) of CQ, CMQ, or DMSO in either normal or reduced pH growth media. Each dose was performed in a minimum of triplicate. Cells were then incubated in the presence of test compounds for 72 hours without media or drug refreshment. Viability was measured by the CellTiter 96 AQueous Non-Radioactive Cell Proliferation Assay (Promega, Madison, Wis.) according to manufacturer's instruction. Briefly, 20 µL of MTS/PMS reagent was added to each tissue culture well, and incubated at 37° C. for a minimum of 2 hours, or until the maximum absorbance at 490 nm on the plate (wells with highest cell numbers) reached a value greater than 0.6. Absorbance was measured on a Perkin-Elmer Victor X4 multi-label plate reader. Absorbance data was fit to a four parameter inhibitor response model using Prism software (GraphPad Software, La Jolla, Calif.) to obtain $IC_{50}$ values and normalization parameters. Statistical analyses were also performed using Prism software.

Results. Cytotoxicity of CMQ compared to CQ. To assess the efficacy of CMQ as a cytotoxic inhibitor of autophagy, we selected a panel of human cancer cell lines for their compatibility with RPM-1640, a growth medium containing lower glucose content than other common growth base media, and systematically treated them with a range of doses of CMQ and CQ. FIG. 5A shows the cytotoxicity profiles of both drugs tested. The normal prostate epithelial cell line, RWPE-1, was included to show relative sensitivity compared to transformed cell lines. As can be seen in all panels of FIG. 5A, and summarized in FIG. 5B, CMQ exhibited more potent cytotoxicity than CQ. RWPE-1 was most resistant to both CQ and CMQ exposure, suggesting that transformed cells are more dependent upon autophagy than their non-transformed counterparts. However, we cannot rule out differences in sensitivity being owed to differences in the formulations in the growth media employed. A correlation analysis of $pIC_{50}$ values obtained for both CQ and CMQ (FIG. 5C) shows that those cells most sensitive to CQ exposure (high $pIC_{50}$) were similarly most sensitive to CMQ, and those most resistant to CQ (low $pIC_{50}$) were also most resistant to CMQ.

Figure 5:
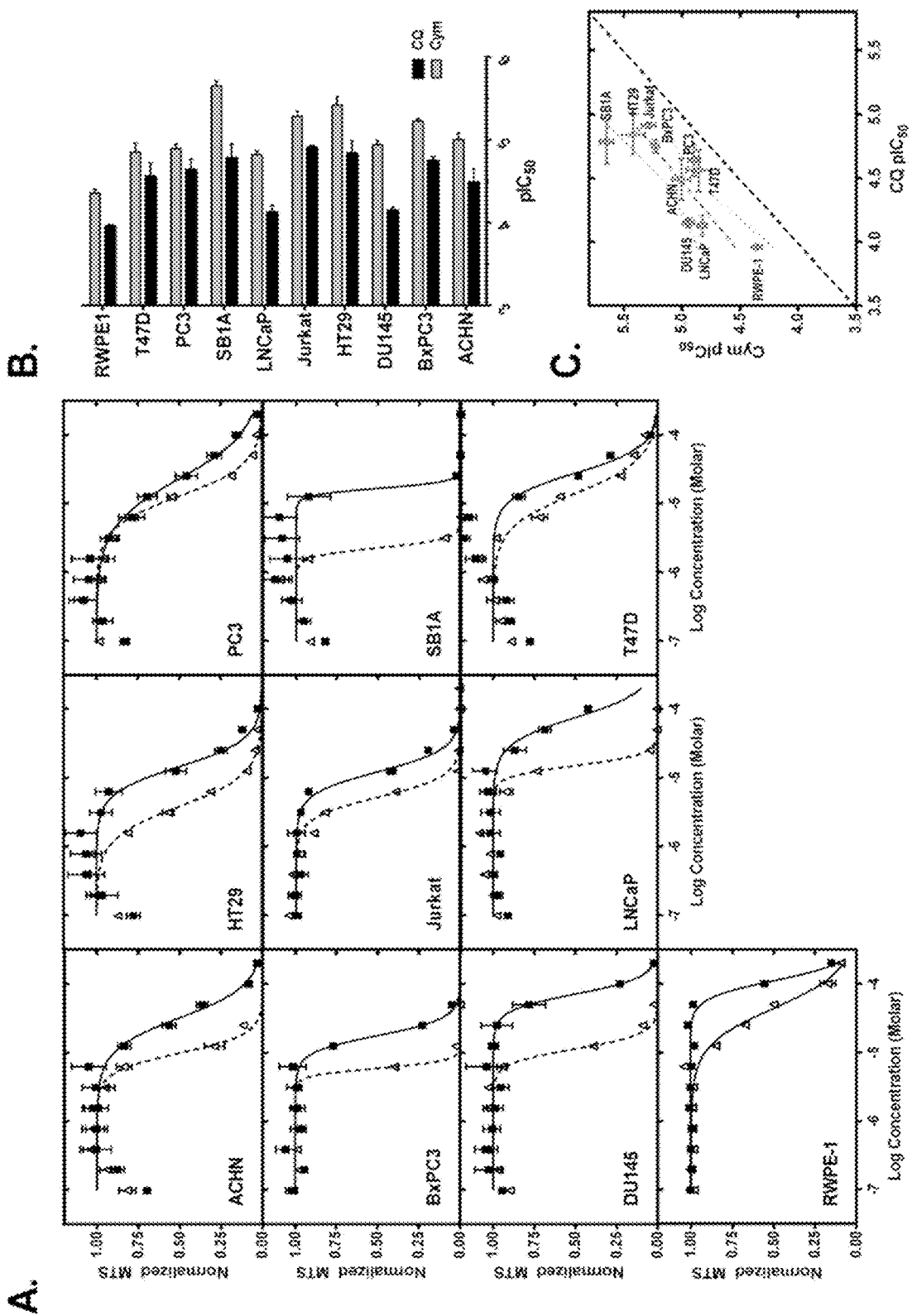
FIG. 5. CMQ, (3) exhibits more potent single-agent cytotoxic properties than CQ in a diverse panel of human cancer cell lines. A, Dose-response cell viability assay for RPMI-compatible human cancer cell lines, and the normal prostate epithelial cell line, RWPE-1, exposed to CMQ (open triangles) and CQ (closed squares) for 72 h (h=hours) under normal pH growth conditions (mean+/−SEM, n=4). Lines represent best fits of data seats to a four parameter inhibitor response model from which $IC_{50}$ values and normalization parameters were determined. B, Compilation of $pIC_{50}$ values obtained by 72 h exposure of multiple human cancer cell lines to CMQ and CQ. Bars represent best-fit $pIC_{50}$ value, error bars represent 95% confidence interval. C, Correlation plot of CMQ $pIC_{50}$ values versus CQ $pIC_{50}$ values. Black dashed line represents unity (no change), solid grey line represents linear regression of the data, with the dashed grey lines representing the 95% confidence boundaries. Pearson correlation analysis revealed a high level of correlation (r=0.8237, P=0.0034), suggesting the compounds share a similar mechanism of action in all cell lines tested.
Figure 6:
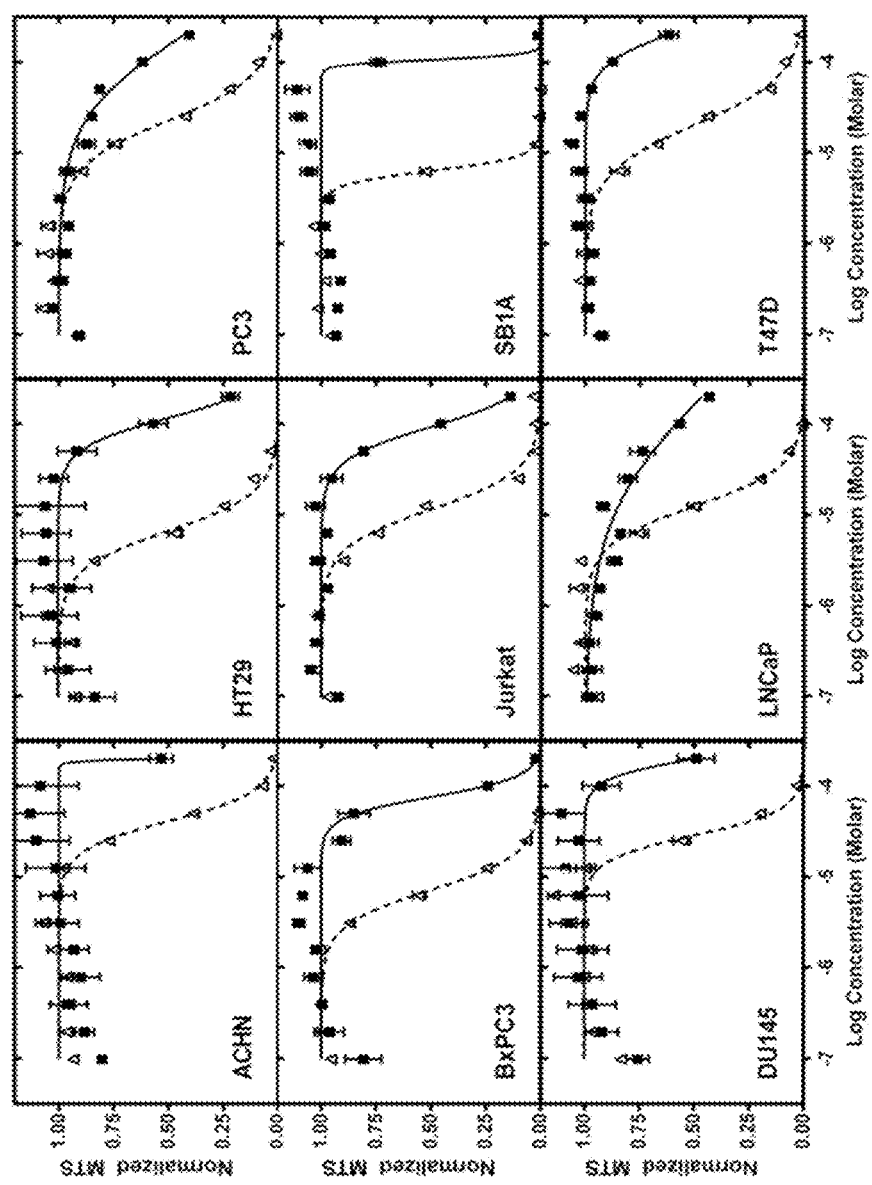
FIG. 6. CMQ exhibits more potent cytotoxicity than CQ under low-pH conditions. A, Dose-response cell viability assay for cell lines grown in low-pH (PIPES-supplemented) media, and exposed to various concentrations of CMQ (open triangles and CQ (closed squares) for 72 h (mean+/−SEM, n=4). Lines represent best fits of data to a four parameter inhibitor response model from which $IC_{50}$ values and normalization parameters were determined. B, Compilation of $pIC_{50}$ values obtained by 72 h exposure of multiple human cancer cell lines to CMQ and CQ under low-pH conditions. Bars represent best-fit $pIC_{50}$ value, error bars represent 95% confidence interval, and #indicates poor convergence of parameters during non-linear regression (wide confidence intervals). C, Comparison of $pIC_{50}$ values obtained by 72 h exposure of multiple human cancer cell lines to CMQ and CQ under normal and low-pH conditions. Lines represent means and quartile ranges. P<0.01, *P<0.005 by Wilcoxon matched pairs signed rank test.

It has been shown previously that, due to its nature as a weak base and reduced bioavailability in the protonated state, CQ exhibits poor anti-autophagic efficacy in low pH media, a proxy for the tumor microenvironment, as well as in bulky tumors in vivo (Pellegrini et al., Autophagy, 2014, 10(4)). To examine if novel organometallic substitutions on the quinoline framework could confer low pH efficacy, we tested the cytotoxicity profiles of CQ and CMQ in the aforementioned human cancer cell line panel. Again, as can be seen in all panels of FIG. 6A, and summarized in FIG. 6B, CMQ exhibits more potent cytotoxicity than CQ in low pH media, as indicated by higher $pIC_{50}$ values obtained. It should be noted, however, that both compounds exhibited reduced efficacy, compared to what was observed in normal pH conditions (FIG. 5). Nevertheless, CMQ consistently displays more potent cytotoxicity in all of the cell lines tested, regardless of the condition employed, as shown in FIG. 6C. These findings suggest that CMQ may be more suitable and effective for treatment of bulky tumors engaging hypoxic metabolism that results in lactic acid accumulation.

Figure 10:
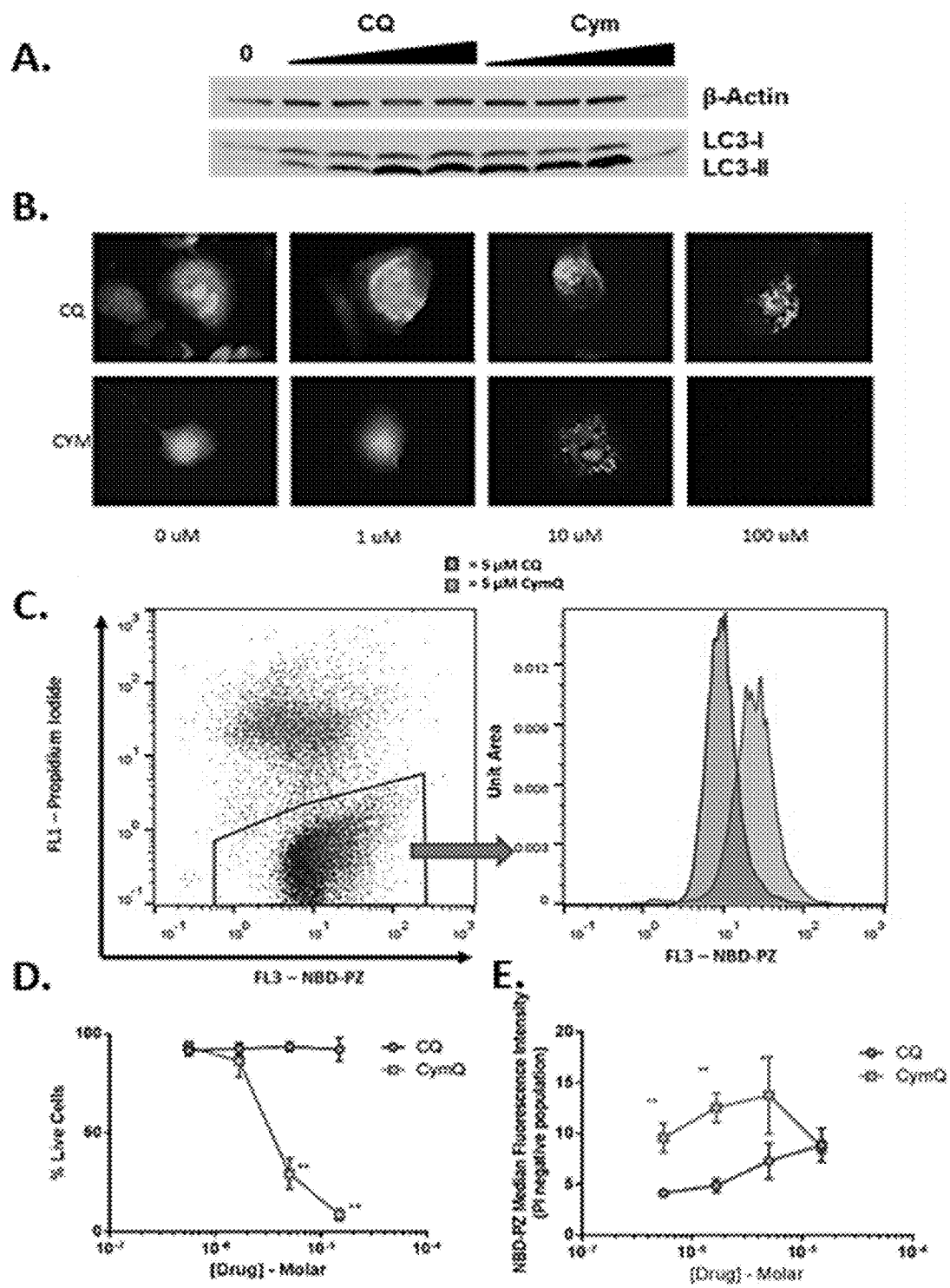
FIG. 10. Evidence of lysosomal accumulation and cytotoxicity obtained through autophagy blockade by Cymanquine. A, SB1A cells were treated with various concentrations of Cymanquine or CQ for 24 h prior to western blotting for LC3 isoforms 1 and 2 (LC3-I and II—see text), respectively. Equal loading for the highest Cymanquine concentration was not possible due to extensive cell death. B, SB1A cells stably expressing EGFP-LC3 were treated with indicated concentrations of CQ and Cymanquine for 4 h prior to fluorescence microscopy evaluation of EGFP-LC3 sub-cellular deposition. C-E, SB1A were treated with various concentrations of Cymanquine or CQ for 24 h prior to simultaneous staining with NBD-PZ and propidium iodide and analysis by flow cytometry. C, Live cells, sorted based on absence of propidium iodide staining (left panel, pentagonal gate) were analyzed for NBD-PZ staining, indicative of lysosomal content. B,C, The dose-response of Cymanquine and CQ on B, percentage of live cells (negative for propidium iodide staining), and C, NBD-PZ median fluorescence intensity of live cells. Data in B,C presented as mean+/−SEM (n=3). *P<0.05, **P<0.001 by student's t-test.

Experiments aimed at elucidating the mechanism of action of Cymanquine were conducted. These experiments showed that this compound enforces autophagy blockade to achieve cytotoxicity in a manner similar, yet superior to CQ. It is known that the blockade of autophagy results in the accumulation of neutralized lysosomes and of proteins normally cleared by autophagic flux. FIG. 10 presents data that support a mechanism of action for Cymanquine as a weak base lysosomotropic autophagy inhibitor. Cymanquine treatment of the aggressive human melanoma cell line SB1A results in dose-responsive accumulation of the autophagy marker protein microtubule associated protein light chain 3 isoform 2 (LC3-II) in a manner similar to CQ treatment, as detected by western blot (FIG. 10A). The highest Cymanquine concentrations tested resulted in extensive cell death. Additionally, Cymanquine treatment also causes alterations in the subcellular distribution of an EGFP-LC3 fusion protein (FIG. 10B), leading to punctate EGFP-LC3 emission patterns characteristic of autophagy blockade. The lysosomotropic fluorophore, NBD-PZ, was employed in conjunction with propidium iodide (PI) to simultaneously measure lysosomal accumulation, neutralization, and cell viability by flow cytometry on CQ and Cym treated SB1A cells (FIG. 10C-E). FIG. 10C shows the systematic gating algorithm we employed for analyzing cell viability and lysosome content. This analysis shows that low micromolar exposures of Cym, and not CQ, cause significant cytotoxicity to the cells in the 24 h timeframe (FIG. 10D) and not merely cytostatic effects, and that cytotoxicity is accompanied by marked accumulation of lysosomes (FIG. 10E). Furthermore, at the highest concentration of Cymanquine tested, NBD-PZ staining is reduced, due to either lysosome loss, or neutralization, as emission of this fluorophore is highly dependent upon pH. Preliminary quantitation of Cymanquine and CQ from isolated lysosomes of cells treated with equimolar quantities of either drug have been encouraging, showing a 60-fold higher accumulation of Cymanquine compared to CQ, as measured by HPLC-MS/MS. This evidence supports the notion that Cymanquine induces cytotoxicity by mechanisms similar to those established for CQ, and demonstrates the feasibility of using LC3 western blotting from xenograft samples to assess extent of autophagy blockade, and HPLC-MS/MS as a means to measure Cymanquine concentrations within the lysosomal compartment of xenograft tumors treated with the drug.

While the invention has been described through illustrative examples, routine modifications of the various embodiments will be apparent to those skilled in the art and such modifications are intended to be within the scope of this disclosure.

What is claimed is:

1. A method for treating carcinomas/sarcomas of the brain, breast, pancreas, prostate, colon, kidney, and skin; leukemia; and combinations thereof comprising administering to an individual who has been diagnosed with, is suffering from, or is at risk of developing cancer, comprising administering to the individual a therapeutically effective amount of a composition comprising one or more compounds having the formula:

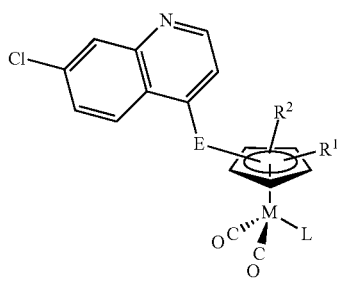

wherein:

M is Mn or Re,

L is a neutral, two-electron donor ligand, $R^1$ is an amine-substituted alkyl group, $R^2$ is H, $(CH_2)_nCH_3$, wherein n is 0 to 20, OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety.

2. The method of claim 1, further comprising subjecting the individual to one or more of the following:

i) surgically removing a malignant tumor, ii) radiation, and iii) additional chemotherapy.

3. The method of claim 1, wherein the composition further comprises a pharmaceutical carrier.

4. A method for inhibiting the growth of cells comprising contacting the cells with a compound having the formula:

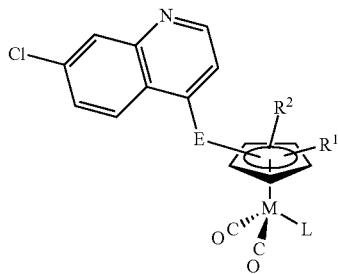

wherein:

M is Mn or Re,

L is a neutral, two-electron donor ligand, $R^1$ is an amine-substituted alkyl group, $R^2$ is H, $(CH_2)_nCH_3$, wherein n is 0 to 20, OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety.

5. The method of claim 4, wherein the compound is present in a pharmaceutical carrier.

6. A kit comprising one or more containers or packaging having instructions for use and one or more compounds having the formula:

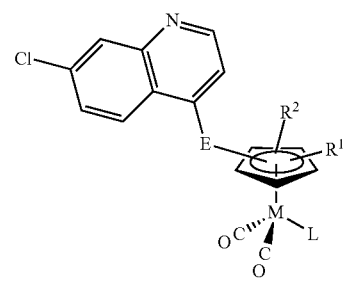

wherein:

M is Mn or Re,

L is a neutral, two-electron donor ligand, $R^1$ is an amine-substituted alkyl group, $R^2$ is H, $(CH_2)_nCH_3$, wherein n is 0 to 20, OMe, OEt, OPh, Ph, CHO, COMe, COPh, $CH_2OH$, $CO_2H$, $CO_2Me$, $CO_2Et$, $CH_2Ph$, $NH_2$, $NMe_2$, $NEt_2$, $C_6H_4Me$, $C_6H_4OMe$, $NH_2COMe$, F, Cl, Br, or I; and E is a linker moiety connecting the cyclopentadienyl moiety with the chloroquinoline moiety.

7. The kit of claim 6, wherein the kit comprises a plurality of individualized sealed packets, each individual packet representing a dose of the composition for a single use.

8. The kit of claim 6, further comprising a pharmaceutical carrier.

9. The kit of claim 8, wherein the kit comprises a plurality of individualized sealed packets, each individual packet representing a dose of the composition for a single use.

10. The method of claim 1, wherein M is Mn.

11. The method of claim 1, wherein M is Re.

12. The method of claim 1, wherein the compound has the following structure:

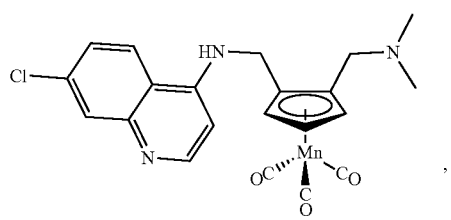

,

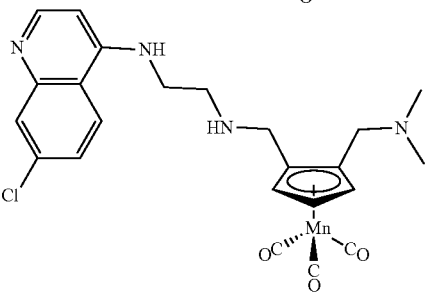

,

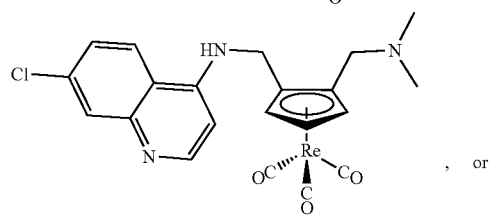

, or

-continued
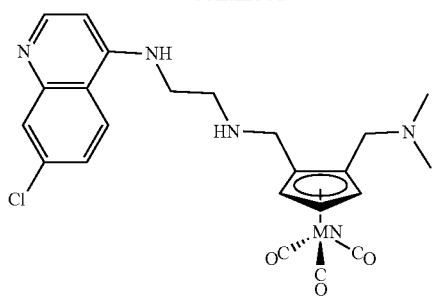
13. The method of claim 4, wherein M is Mn.
14. The method of claim 4, wherein M is Re.
15. The method of claim 4, wherein the compound has the following structure:
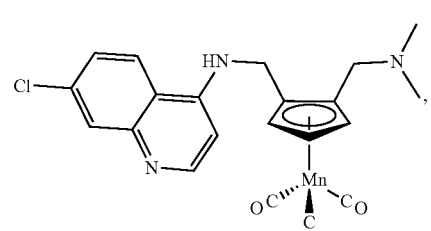
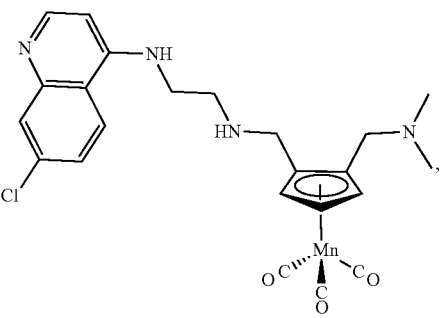
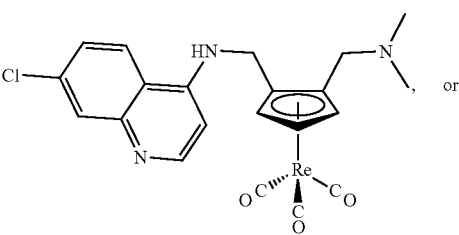
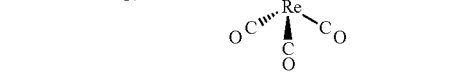
-continued
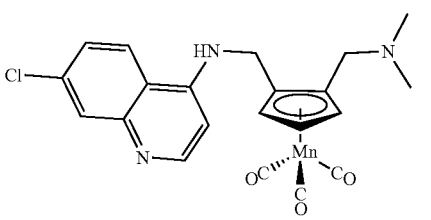
16. The kit of claim 6, wherein M is Mn.
17. The kit of claim 6, wherein M is Re.
18. The kit of claim 6, wherein the compound has the following structure:
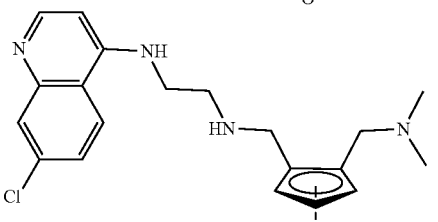
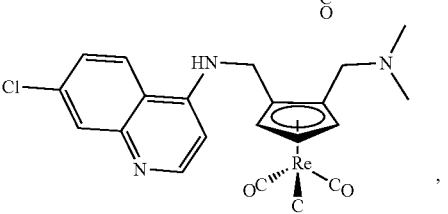
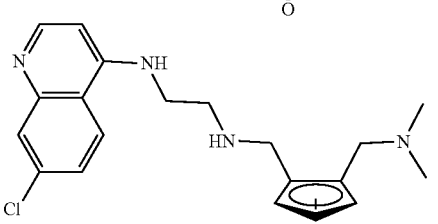
* * * * *